United States Patent [19]

Coates et al.

[11] Patent Number: 5,482,653
[45] Date of Patent: Jan. 9, 1996

[54] FLUORO-CHLORO-BENZENE DERIVATIVES

[75] Inventors: David Coates, Merley; Ian C. Sage, Broadstone; Simon Greenfield, Creekmore; Graham Smith, Poole; David W. Baxter, Wistaton, all of Great Britain

[73] Assignee: Merck Patent Gesellschaft Mit Beschrankter Haftung, Darmstadt, Germany

[21] Appl. No.: 902,801

[22] Filed: Jun. 24, 1992

Related U.S. Application Data

[63] Continuation of Ser. No. 572,976, Jul. 31, 1990, abandoned.

[30] Foreign Application Priority Data

May 30, 1989 [GB] United Kingdom ............... 8912339
Jun. 12, 1989 [GB] United Kingdom ............... 8913441
Jun. 12, 1989 [GB] United Kingdom ............... 8913442

[51] Int. Cl.$^6$ .................... C09K 19/30; C09K 19/12; C07C 19/08
[52] U.S. Cl. .................... 252/299.63; 252/299.66; 570/129
[58] Field of Search .................... 252/299.63, 299.66; 570/129

[56] References Cited

U.S. PATENT DOCUMENTS

| | | | |
|---|---|---|---|
| 4,400,293 | 8/1983 | Romer et al. | 252/299.63 |
| 4,405,488 | 9/1983 | Sugimori et al. | 252/299.63 |
| 4,480,305 | 12/1984 | Eidenschink et al. | 260/465 F |
| 4,620,938 | 11/1986 | Romer et al. | 252/299.63 |
| 4,710,315 | 12/1987 | Schad et al. | 252/299.63 |
| 4,797,228 | 1/1989 | Goto et al. | 252/299.63 |
| 4,846,998 | 7/1989 | Pohl et al. | 252/299.63 |
| 4,886,621 | 12/1989 | Sage et al. | 252/299.61 |
| 4,917,819 | 4/1990 | Goto et al. | 252/299.63 |

FOREIGN PATENT DOCUMENTS

| | | |
|---|---|---|
| 3902328 | 8/1990 | Germany. |
| 60-56932 | 4/1985 | Japan. |
| 2086385 | 5/1982 | United Kingdom. |
| 8603769 | 7/1986 | WIPO. |
| 8809360 | 12/1988 | WIPO. |

Primary Examiner—Robert L. Stoll
Assistant Examiner—C. Harris

[57] ABSTRACT

The invention relates to fluoro-chloro-benzene derivatives of the formula I $$R-A-Q-\text{(phenyl with }L^1, L^2\text{)}-Cl \quad I$$

wherein

R denotes an alkyl or halogenoalkyl residue of up to 12 C atoms wherein one or two non-adjacent $CH_2$ groups may also be replaced by -O- and/or -HC=CH-,
the radical A is a ring of the formula (1) or (2):

(1) cyclohexylene(H)    (2) phenylene with $L^0$

Q is a bivalent radical of the formula (1) or (2) or a single bond or—if radical A denotes trans-1,4-cyclohexylene—is also a bivalent radical of the formulae (3), (4) or (5):

(3) phenyl($L^0$)—$CH_2CH_2$—

(4) —$CH_2CH_2$—phenyl($L^0$)—

(5) cyclohexyl($L^0$)—$CH_2CH_2$—phenyl— and $L^0$, $L^1$ and $L^2$ are each independently H or F, with the proviso that at least one of $L^0$, $L^1$ and $L^2$ present in the molecule denotes F.

9 Claims, No Drawings

FLUORO-CHLORO-BENZENE DERIVATIVES

This application is a continuation of application Ser. No. 07/572,976, filed Jul. 31, 1990, now abandoned.

The invention relates to fluoro-chloro-benzene derivatives of the formula I

Fluoro-chloro-benzene derivatives of the formula I

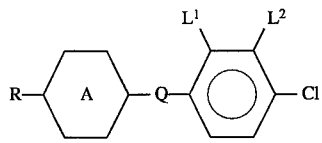

wherein
R denotes an alkyl or halogenoalkyl residue of up to 12 C atoms wherein one or two non-adjacent $CH_2$ groups may also be replaced by -O- and/or -HC=CH-,
the radical A is a ring of the formula (1) or (2):

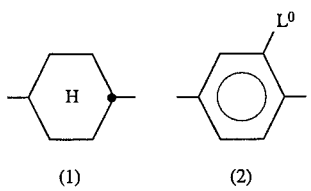

Q is a bivalent radical of the formula (1) or (2) or a single bond or—if radical A denotes trans-1,4-cyclohexylene—is also a bivalent radical of the formulae (3), (4) or (5):

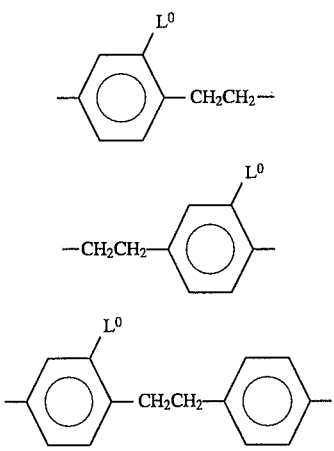

and $L°$, $L^1$ and $L^2$ are each independently H or F, with the proviso that at least one of $L°$, $L^1$ and $L^2$ present in the molecule denotes F, and also to liquid crystalline media being a mixture of at least 2 compounds, characterized in that at least one compound is a fluorinated benzene derivative according to formula I.

The invention was based on the object of discovering new stable liquid crystal or mesogenic compounds which are suitable as components of liquid crystalline media and, in particular, have advantageous values for optical and dielectric anisotropy combined with low viscosity and high nematogenity.

Similar chloro-benzene derivatives without lateral fluorine substitution are described in DE 31 36 624, DE 31 39 130, JP 571183727 and JP 59/81375 and also by S. M. Kelly and Hp. Schad, Helv. Chim. Acta 68 (5), 1444–52 (1985) and H. Takatsu et al., Mol. Cryst. Liq. Cryst. 100 (3–4), 345–55 (1983).

It has now been found that laterally fluorinated compounds of formula I are highly suitable as polar components of liquid crystalline media. In particular, they have especially advantageous values of optical and dielectric anisotropy and are not strongly smectogenic. It is also possible to obtain stable liquid crystal phases with a broad nematic mesophase range including a good deep temperature behaviour, a high resistivity and a comparatively low viscosity with the aid of these compounds.

Depending on the choice of R, A, Q, $L^1$ and $L^2$ the compounds of the formula I can be used as the base materials from which liquid crystal media are predominantly composed; however, it is also possible for compounds of the formula I to be added to liquid crystal base materials of other classes of compounds, for example in order to influence the dielectric and/or optical anisotropy and/or the viscosity and/or the nematic mesophase range of such a dielectric.

The compounds of the formula I are colourless in the pure state and are liquid crystalline in a temperature range which is favourably placed for electrooptical use. They are very stable towards chemicals, heat and light.

The invention thus relates to the benzene derivatives of the formula I, to liquid crystalline media with at least two liquid crystalline components, wherein at least on component is a compound of the formula I and to liquid crystal display devices containing such media.

Above and below, R, A, Q, $L^1$ and $L^2$ have the meaning given unless expressly indicated otherwise.

The compounds of the formula I include benzene derivatives of the formulae Ia to Ig:

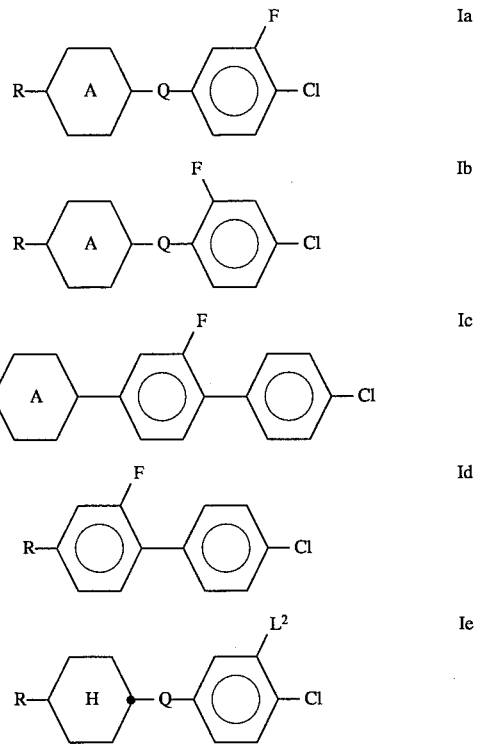

-continued

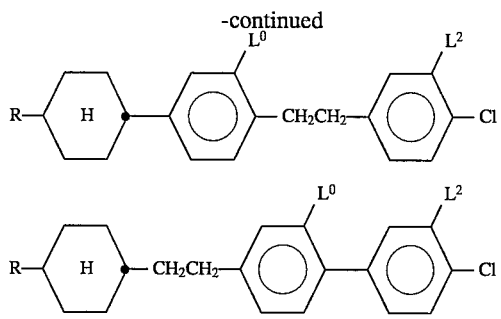

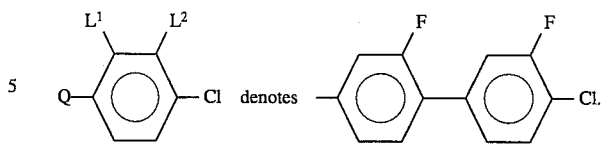

In formula Ib Q is preferably trans-1,4-cyclohexylene or 1,4-phenylene. In formula Ie 0 is a bivalent radical of formula (3), (4) or (5).

R is preferably alkyl, alkoxy, oxaalkyl or alkenyl and can exhibit a straight-chain or branched structure.

Alkyl or alkoxy preferably are straight-chain and have 2, 3, 4, 5, 6 or 7 C. atoms. Accordingly they are preferably ethyl, propyl, butyl, pentyl, beryl, heptyl, ethoxy, propoxy, butoxy, penfoxy, hexory or heptoxy, also methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

Oxaalkyl is preferably straight-chain 2-oxapropyl (=methoxymethyl). 2-(=ethoxymethyl) or 3-oxybutyl (=2-methoryethyl), 2-, 3- or 4-oxapentyl, 2-, 3-, 4- or 5-oxahexyl, 2-, 3-, 4- 5- or 6-oxaheptyl, 2-, 3-, 4-, 5-, 6- or 7-oxaoctyl, 2-, 3-, 4-, 5-, 6-, 7-or 8-oxanonyl or 2-, 3-, 4-, 5-, 6-, 7-, 8-, or 9-oxadecyl.

Alkenyl is preferably straight-chain and has 2 or 10 C atoms. It is accordingly, in particular, vinyl, prop-1- or prop-2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or-6-enyl, oct-1-, -2-, -3-, -4-, -5- -6- or -7-enyl, non-1-, -2-, -3-, -4-, -5-, -6-, -7- or -8-enyl or dec-1-, -2-, -3-, -4-, -5-, -6-, -7-, -8- or-9-enyl.

Halogenoalkyl is preferably an alkyl residue (preferably straight-chained) carrying a fluoro or chloro substituent on one of the up to 12 carbon atoms.

Compounds of the formula I containing a branched terminal group can occasionally be of importance because of an improved solubility in the customary liquid crystal base materials, but in particular as chiral doping substances if they are optically active.

Branched groups of this type as a rule contain not more than one chain branching. Preferred branched radicals are isopropyl, 2-butyl (=1-methylpropyl), isobutyl (=2-methylpropyl, 2-methylbutyl, isopentyl, (=3-methylburyl), 2-methylpentyl, 2-ethylhexyl, 2-propylpentyl; 2-octyl, isopropoxy, 2-methylpropoxy, 2-methylbutoxy, 3-methylbutoxy, 2-methylpentoxy, 3-methylpentoxy, 2-ethylhexoxy, 2-methylhexoxy, 1-methylhexoxy, 1-methylheptoxy (=2-octyloxy), 2-oxa-3-methylbutyl, 3-oxa-4-methylpentyl, 4-methylhexyl, 2-nonyl, 2-decyl, 2-dodecyl, 6-methyloctoxy, oxy, 2-methyl-3-oxapentyl and 2-methyl-3-oxahexyl.

In the case of compounds with a branched terminal group R, formula I includes both the optical antipodes and racemates as well as mixtures thereof.

Preferably only one of the substituent $L^0$, $L^1$ and $L^2$ present in the molecule deno tes F. Furthermore preferred are those compounds of the formula I wherein Of the compounds of the formula I and subformulae thereof, those in which at least one of the radicals contained therein has one of the preferred meanings given are preferred.

The compounds of the formula I are prepared by methods which are .known per se, such as are described in the literature (for example in the standard works, such as Houben-Weyl, Methoden der Organischen Chemic Methods of Organic Chemistry, GeorgThieme Verlag, Stuttgart), and in particular under reaction conditions which are known and suitable for the reactions mentioned. Variants which are known per se and are not mentioned in more detail here can also be used in this connection.

If desired, the starting materials can also be formed in situ, such that they are not isolated from the reaction mixture but are immediately reacted further to give the compounds of the formula I.

Preferred routes for preparation are shown in the following schemes:

Scheme 1

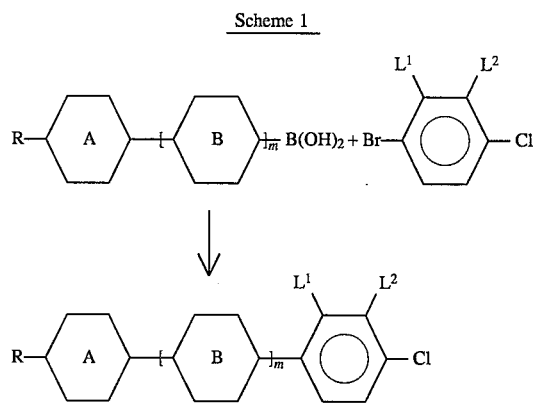

Scheme 2

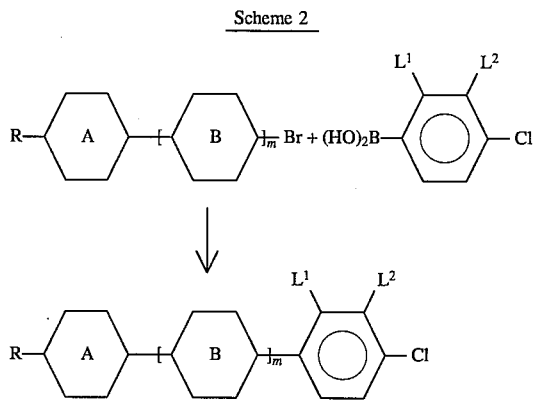

In schemes 1 and 2 ring B denotes a ring of formula (2) and m is 0 or 1.
Scheme 3
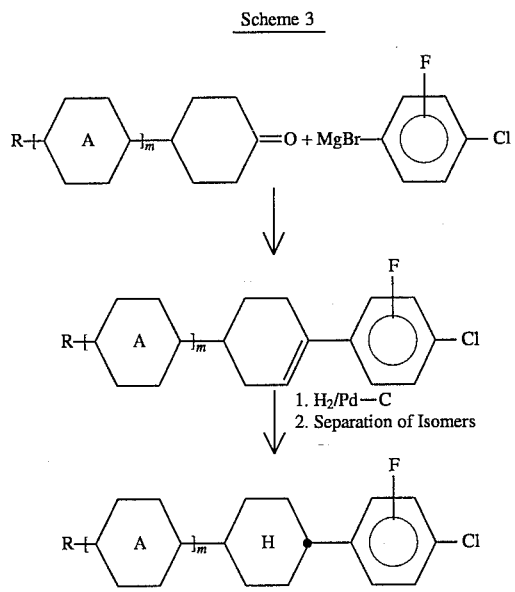
In scheme 3 ring A denotes trans-1,4-cyclohexylene or 1,4-phenylene. trans-1,4-Cyclohexylene is preferred.
Scheme 4
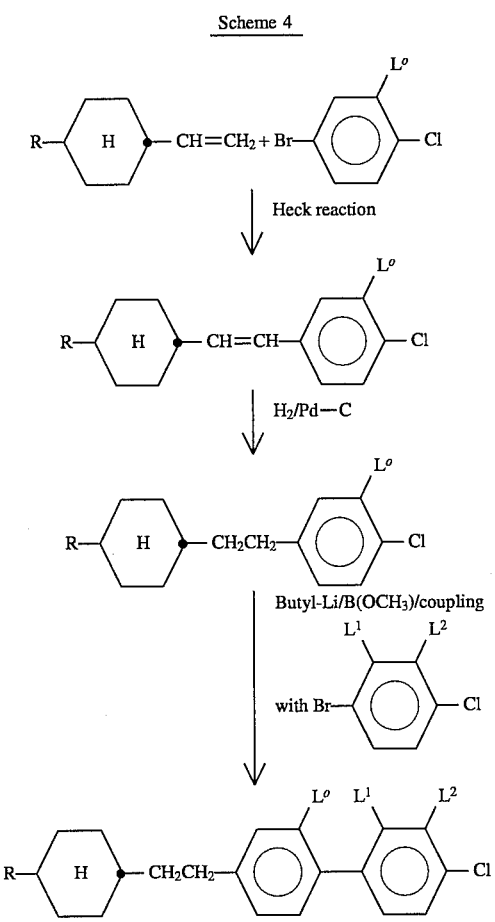
Scheme 5
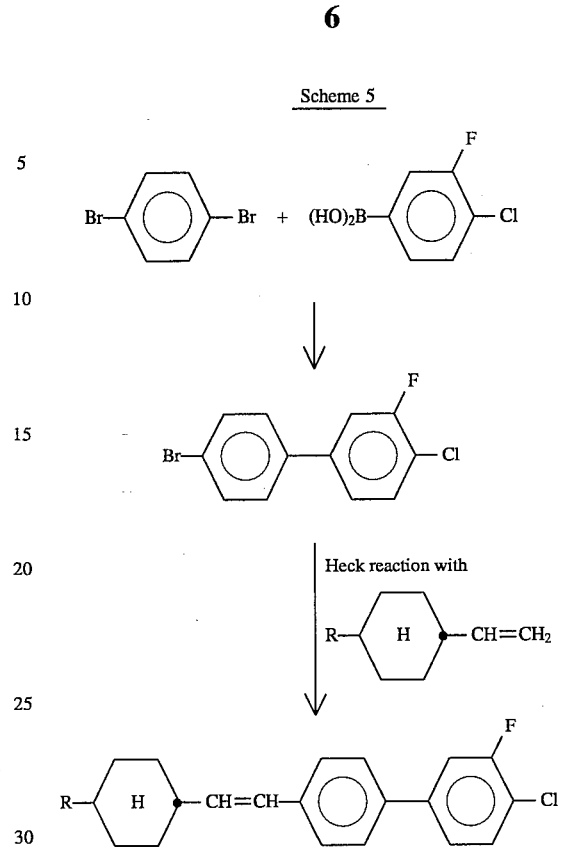
Scheme 6
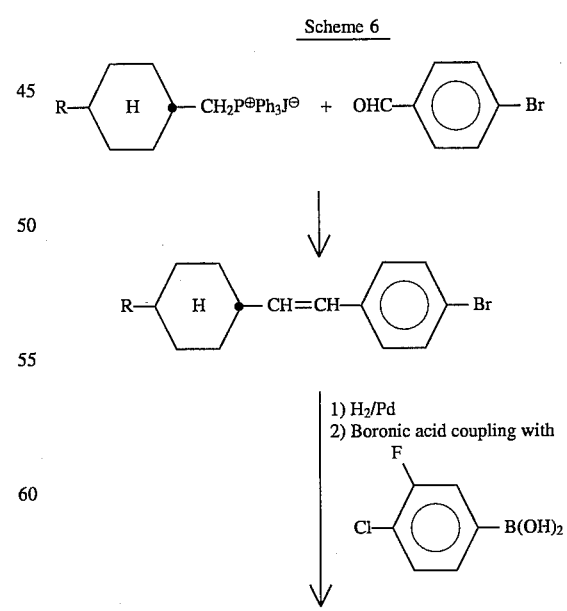

-continued
Scheme 6
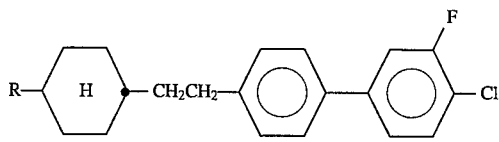
Scheme 7
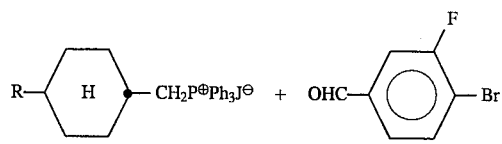
↓ Wittig reaction
↓ H₂/Pd
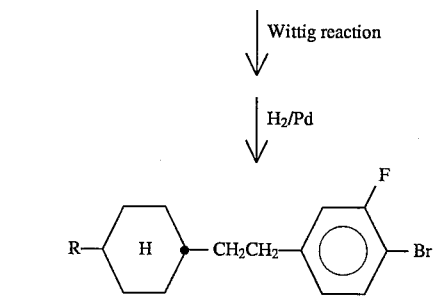
↓ 1. Mg/Grignard reagent
↓ 2. trimethylborate
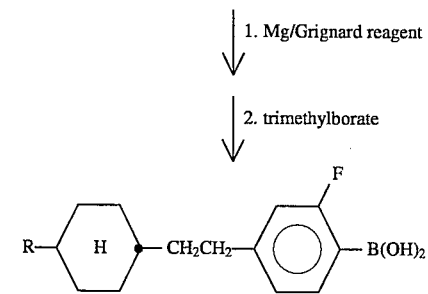
↓ coupling with
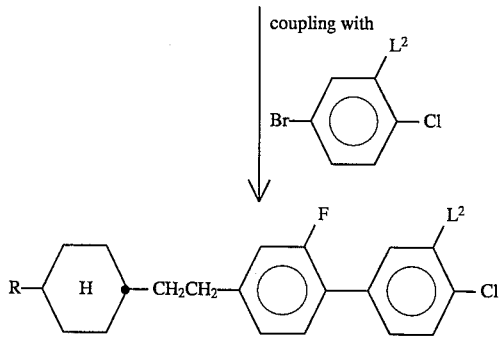
L² = H or F
Scheme 8
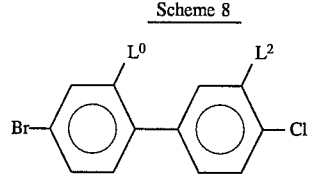
↓ Mg/DMF
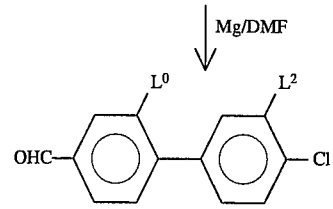
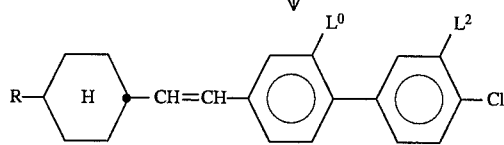
↓ H₂/Pd—C
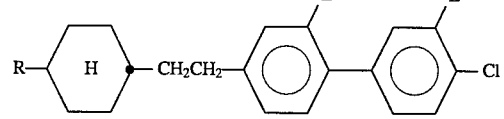
Scheme 9
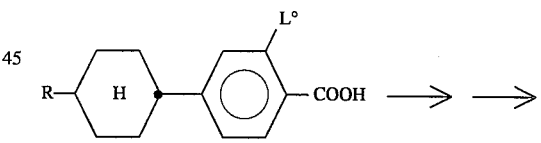
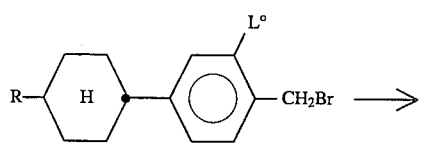

-continued
Scheme 9
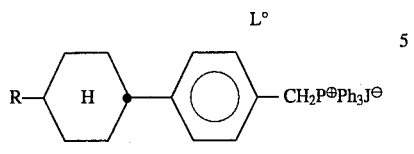
a) OHC—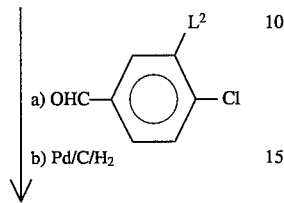—Cl
b) Pd/C/H₂
-continued
Scheme 9
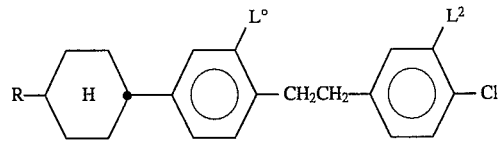
Scheme 10
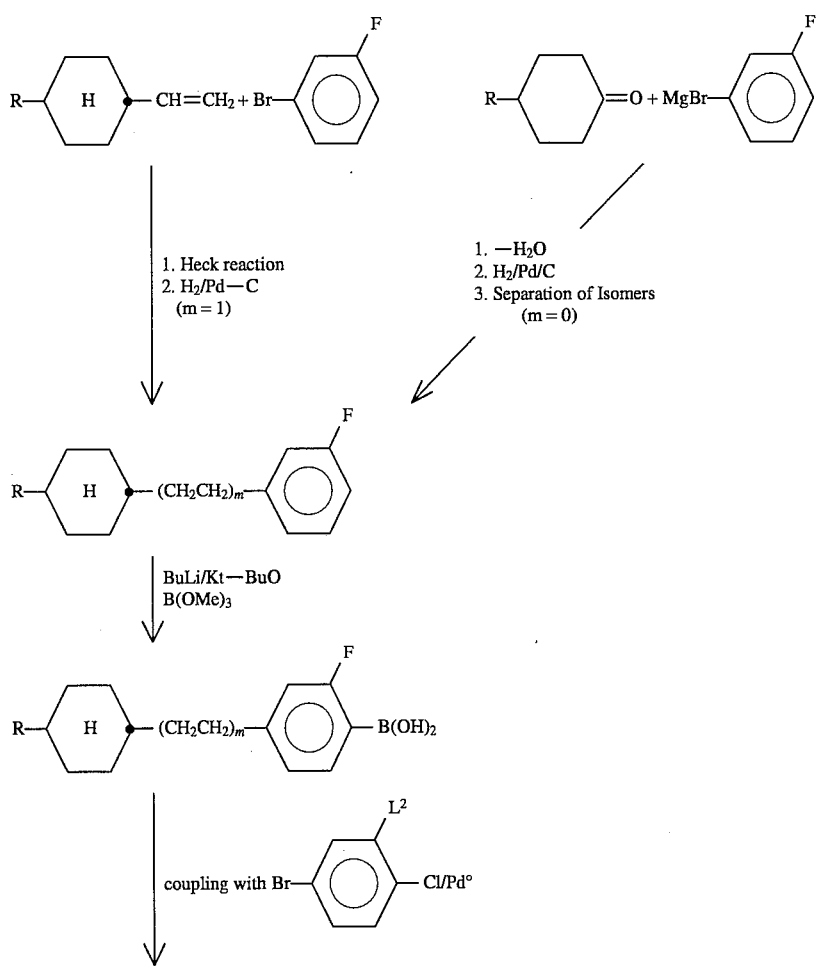

-continued
Scheme 10

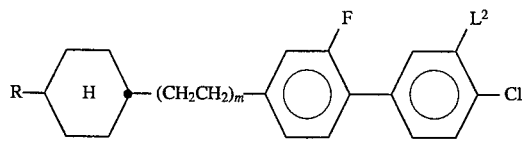

Scheme 11

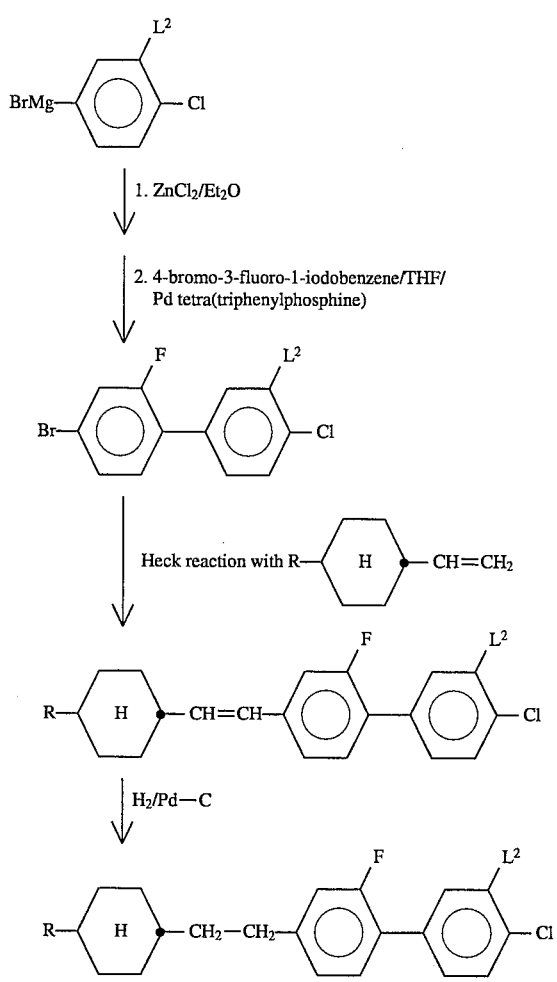

Scheme 12

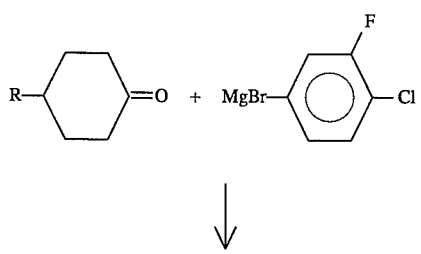

-continued
Scheme 12

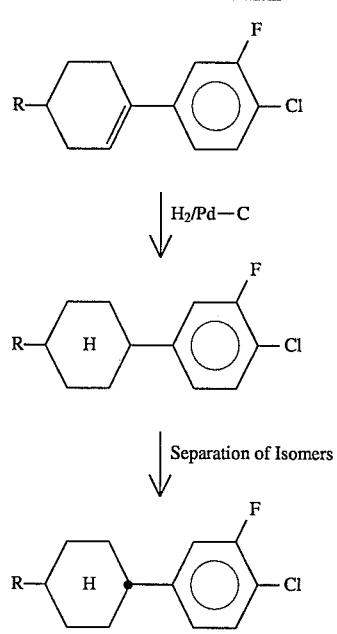

All starting materials are known or can be prepared in analogy-to known compounds. The alkenes can be made by Heck reaction of cyclohexylbromides and vinyl bromide. The starting acids can be obtained from the known cyano compounds.

4-chloro-2-fluorobromobenzene can be made by diazotisation ad Sandmeyer reaction on 4-chloro-2-fluoroaniline. 4-Bromo-2-fluoroalkylbenzenes are made by the following route:

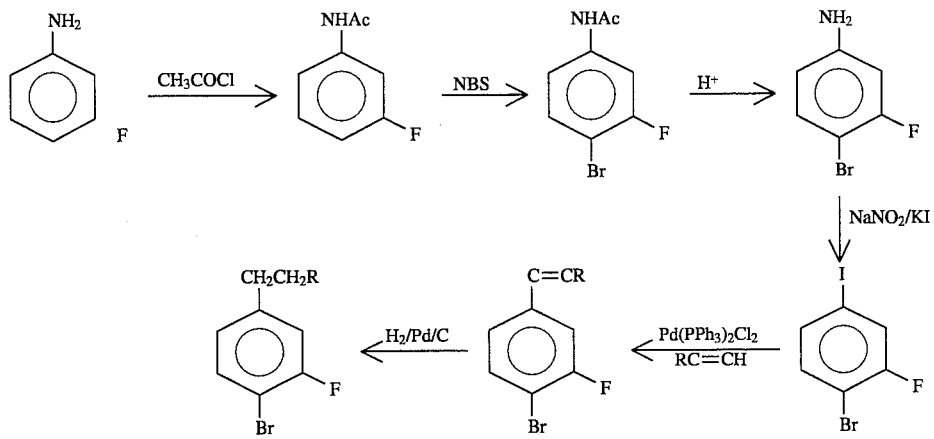

The 2-fluoro-4-bromo-3-$L^2$-4'-chloro-biphenyls ($L^2$=H or F), for example, can be made by transition metal catalyzed cross-coupling reactions (E. Poetsch, Kontakte (Darmstadt) 1988 (2) p. 15):

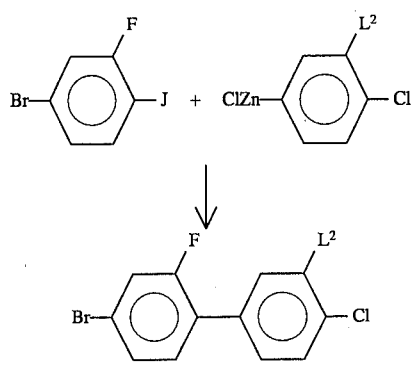

Other routes are apparent to the skilled worker. All these steps and the corresponding reaction conditions are known the skilled worker.

In addition to one or more compounds for formula I the liquid crystal media according to the invention preferably contain 2–40 components and in particular 4–30 components. Liquid crystal media being composed of one or more compounds of formula I and 7–25 other components are especially preferred.

These additional components are preferably chosen from the nematic or nematogenic (monotropic or isotropic) substances; in particular from the classes of azoxybenzenes, benzylideneanilines, biphenyls, terphenyls, phenyl or cyclohexyl benzoates, phenyl or cyclohexyl cyclohexanecarboxylates, phenyl or cyclohexyl cyclohexylbenzoates, phenyl or cyclohexyl cyclohexylcyclohexanecarboxylates, cyclohexylphenylbenzoates, cyclohexylphenyl cyclohexanecarboxylates, cyclohexylphenyl cyclohexylcyclohexanecarboxylates, phenylcyclohexanes, cyclohexylbiphenyls, phenylcyclohexylcyclohexanes, cyclohexylcyclohexanes, cyclohexylcyclohexenes, cyclohexylcyclohexylcyclohexene, 1,4-bis-cyclohexylbenzenes, 4,4'-biscyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenyl-cyclohexyl)-ethanes, 1-cyclohexyl-2-biphenylethanes, 1-phenyl-2-cyclohexyl-phenylethanes, optionally halogenated stilbenes, benzyl phenyl ethers, tolanes and substituted cinnamic acids.

The 1,4-phenylene groups of these compounds may be fluorinated.

The most important compounds which are possible constituents of liquid crystal media according to the invention can be characterized by the formalae 1, 2, 3, 4 and 5:

| | |
|---|---|
| R'—L—U—R" | 1 |
| R'—L—COO—U—R" | 2 |
| R'—L—OOC—U—R" | 3 |
| R'—L—CH$_2$CH$_2$—U—R" | 4 |
| R'—L—CC—U—R" | 5 |

In the formulae 1, 2, 3, 4 and 5 L and U may be equal or different from each other. L and U independently from each other denote a bivalent residue selected from the group consisting of -Phe-, -Cyc-, -Phe-Phe-, -Phe-Cyc-, -Cyc-Cyc-, -Pyr-, -Dio-, -G-Phe-, -G-Cyc- and their mirror images; in this compilation of residues Phe denotes unsubstituted or fluorinated 1,4-phenylen, Cyc trans- 1,4-cyclohexylene or 1,4-cyclohexenylen, Pyr pyrimidine-2,5-diyl or pyridine-2,5-diyl, Dio 1,3-dioxane-2,5-diyl and G 2-(trans-1,4-cyclo-hexyl)-ethyl, pyrimidine-2,5-diy1, pyridine-2,5-diy1 or 1,3-dioxane-2,5-diyl.

One of the residues L and U is preferably Cyc, Phe or Pyr. U preferably denotes Cyc, Phe or Phe-Cyc. The liquid crystal media according to the invention preferably contain one or more components selected from the compounds of formulae 1, 2, 3, 4 and 5 with L and U meaning Cyc, Phe and Pyr, said liquid crystal media further containing at the same time one ore more components selected from the compounds of formulae 1, 2, 3, 4 and 5 with one of the residues L and U denoting Cyc, Phe and Pyr and the other residue being selected from the group consisting of -Phe-Phe-, -Phe-Cyc-, -Cyc-Cyc-, -G-Cyc-, said liquid crystal media containing in addition to this optionally one or more components selected from the compounds of formulae 1, 2, 3, 4 and 5 with L and U being selected from the group consisting of -Phe-Cyc-, -Cyc-Cyc-, -G-Phe- and -G-Cyc.

In a preferred subgroup of the compounds of formulae 1, 2, 3, 4 and 5 (subgroup 1) R' and R" are independently from each other alkyl, alkenyl, alkoxy, alkenoxy with up to 8 carbon atoms. R' and R" differ from one another in most of these compounds, one of the residues usually being alkyl or alkenyl. In another preferred subgroup of the compounds of formulae 1, 2, 3, 4 and 5 (subgroup 2) R" denotes -CN, -CF$_3$, -F, -Cl or -NCS while R' has the meaning indicated in subgroup 1 and is preferably alkyl or alkenyl. Other variants of the envisaged substituents in the compounds of formulae 1, 2, 3, 4 and 5 are also customary. Many such substances are commercially available. All these substances are obtainable by methods which are known from the literature or by analogous methods.

The liquid crystal media according to the invention preferably contain in addition to components selected from subgroup 1 also components of subgroup 2, the percentage of these components being as follows:
subgroup 1: 20 to 90%, in particular 30 to 90%
subgroup 2: 10 to 50%, in particular 10 to 50%

In these liquid crystal media the percentages of the compounds according to the invention and the compounds of subgroup 1 and 2 may add up to give 100%.

The media according to the invention preferably contain 1 to 40%, in particular 5 to 30% of the compounds according to the invention. Media containing more than 40%, in particular 45 to 90% of the compounds according to the invention are further preferred. The media contain preferably 3, 4 or 5 compounds according to the invention.

The media according to the invention are prepared in a manner which is customary per se. As a rule, the components are dissolved in one another, advantageously at elevated temperature. The liquid crystal media according to the invention can be modified by suitable additives so that they can be used in all the types of liquid crystal display devices. Such additives are known to the expert and are described in detail in the literature (H. Kelker/R. Hatz, Handbook of Liquid Crystals, Verlag Chemie, Weinheim, 1980).

For example, it is possible to add pleochroic dyestuffs to prepare colored guest-host systems or substances for modifying the dielectric anisotropy, the viscosity and/or the orientation of the nematic phases.

The following examples are to be construed as merely illustrative and not limitative. m.p. =melting point, c.p. =clearing point. In the foregoing and in the following all parts and percentages are by weight and the temperatures are set forth in degrees Celsius. "Customary work-up" means that water is added, the mixture is extracted with methylene chloride, the organic phase is seperated off, dried and evaporated, and the produce is purified by crystallization and/or chromatography.

Further are:
C: crystalline-solid state, S: smectic phase (the index denoting the typ of smectic phase), N: nematic phase, Ch: cholesteric phase, I: isotropic phase. The number being embraced by 2 of these symbols denotes the temperature of phase change.

EXAMPLE 1

A mixture of 0.1 mole of 4'-n-propyl-4-biphenylboronic acid (obtained by the reaction of the Grignard reagent of 4'-n-propyl-4-bromobiphenyl and trimethyl borate), 0.1 mole of 4-chloro-3-fluorobromobenzene, tetrakis (triphenylphosphine) palladium (1 mole %), 2 m sodium carbonate solution (150 ml), toluene (250 ml) and IMS (60 ml) is stirred and refluxed for 16 hrs under a nitrogen atomosphere. After usual work-up 4-chloro-3-fluoro-4'-(p-n-propylphenyl) -biphenyl is obtained.

EXAMPLES 2 to 11

In place of the 4'-n-propyl-4-bromobiphenyl the other well known relevant bromo compounds can be used for preparation of the following compounds in analogy to example 1:

$$R-X-\underset{Cl}{\overset{F}{\bigcirc}}$$

| R | X | |
|---|---|---|
| (2) ethyl | —◯—◯— | |
| (3) n-pentyl | —◯—◯— | C 171 $S_A$ 178 N 194 I |
| (4) n-propyl | —(H)—◯— | C 108 N 143.5 I, $\Delta\epsilon = 6.5$ |
| (5) n-pentyl | —(H)—◯— | |
| (6) ethyl | —◯— | |
| (7) n-propyl | —◯— | |
| (8) n-butyl | —◯— | |
| (9) n-pentyl | —◯— | |
| (10) n-heptyl | —◯— | |
| (11) n-nonyl | —◯— | |

EXAMPLE 12

Under the condition described in example 10.1 mole of 4-bromo-2-fluoro-n-pentylbenzene is coupled with 4-chlorophenylboronic acid (made from 4-chlorobromobenzene via the Grignard reagent and trimethyl borate). After usual work-up 4-chloro-2'-fluoro-4'-n-pentylbiphenyl is obtained.

EXAMPLES 13 to 16

The following compounds are prepared analogously:
(13) 4-chloro-2'-fluoro-4'-n-propylbiphenyl
(14) 4-chloro-2'-fluoro-4'-n-hexanoyloxybiphenyl, K24 I
(15) 4-chloro-2'-fluoro-4'-n-heptylbiphenyl
(16) 4-chloro-2'-fluoro-4'-n-nonylbiphenyl

EXAMPLE 17

A solution of 4-n-propylcyclohexanone (0.1 m) in THF is slowly added to a warm solution of 4-chloro-3-fluorophenyl magnesium bromide (0.11 m) (made from 4-chloro-3-fluorobromobenzene) in THF under nitrogen. The resulting alcohol is dehydrated by sulphuric acid.

Hydrogenation of the resulting olefin over Pd/C gives a mixture of cis/trans isomers. 4-(Trans-4-n-propylcyclohexyl)-2-fluoro-1-chlorobenzene is obtained by chromatography and crystallization, C −15 I, $\Delta\epsilon$=5.2.

EXAMPLES 18 to 20

The following compounds are prepared analogously:
(18)  4-(trans-4-n-butylcyclohexyl)-2-fluoro-1-chlorobenzene

(19) 4-(trans-4-n-pentylcyclohexyl)-2-fluoro-1-chlorobenzene, C −3 I, Δε=4.8
(20) 4-(trans-4-n-heptylcyclohexyl)-2-fluoro-1-chlorobenzene

EXAMPLE 21 to 23

The following compounds are obtained analogously by using 4-(trans-4-alkylcyclohexyl)-cyclohexanones as educts:
(21) 4-(trans,trans-4'-ethylbicyclohexyl-4-yl)-2-fluoro-1chlorobenzene
(22) 4-(trans, trans -4'-n-propylbicyclohexyl-4-yl)-2-fluoro-1-chlorobenzene, C 42 N 157.3 I, Δε−7.0
(23) 4-( trans, trans-4'-n-pentylbicyclohexyl-4-yl )-2-fluoro-1-chlorobenzene

EXAMPLE 24

The compound from example 17 is lithiated using butyl lithium at low temperatures by the usual procedure and then converted to a boronic acid by the addition of trimethyl borate at low temperatures by the usual procedure. The boronic acid is the coupled with 4-bromo-chlorobenzene according to example 1.

After usual work-up 4-chloro-2'-fluoro-4'-(trans-4-n-propyl-cyclohexyl)-biphenyl is obtained C 113 N 142.1 I.

EXAMPLES 25 to 27

The following compounds are prepared analogously:
(25) 4-chloro-2'-fluoro-4'-(trans-4-n-butylcyclohexyl)-biphenyl
(26) 4-chloro-2'-fluoro-4'-(trans-4-n-pentylcyclohexyl)-biphenyl C 106 N 145.9 I
(27) 4-chloro-2'-fluoro-4' -(trans-4-n-heptylcyclohexyl)biphenyl

EXAMPLE 28

A mixture of 0.1 mole of 2-fluoro-4-(trans-4-n-propylcyclo-hexylethyl)-phenyl boronic acid (obtained using butyllithium and trimethylborate at low temperatures according to scheme 4), 0.1 mole of 4-bromochlorobenzene, tetrakis(triphenylphosphine)palladium (1 mole 4) 2 m sodium carbonate solution (150 ml), toluene (250 ml) and INS (60ml) is stirred and refluxed for 16 hrs under a nitrogen atmosphere. After cooling the organic layer is separated, washed with water and the solvent evaporated off. The crude 4-(trans-4-propylcyclohexylethyl)-2-fluoro-4'-chlorobiphenyl is purified by chromatography on silica and crystallisation C 72 N 120 I.

EXAMPLES 29 to 33

The following compounds are obtained analogously:

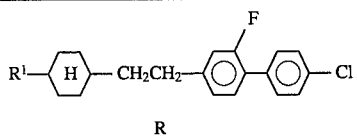

(29) n-pentyl
(30) n-heptyl
(31) n-butyl
(32) n-hexyl
(33) ethyl

EXAMPLE 34

From 1-bromo-4-(trans-4-n-propylcyclohexylethyl)-benzene and 3-fluoro-4-chlorophenylboronic acid (obtained by treating the Grignard reagent of 3-fluoro-4-chloro-bromobenzene with trimethylborate at 20° C.) 4-(trans-4-propylcyclohexyleth-yl)-3'-fluoro-4'-chlorobiphenyl is obtained in analogy to example 1, K 48 $S_A$ 51H 1311.

EXAMPLES 35 to 39

The following compounds are obtained analogously:

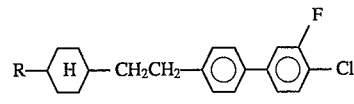

(35) ethyl
(36) n-butyl
(37) n-pentyl
(38) n-hexyl
(39) n-heptyl

EXAMPLE 40

After hydrogenation of 1-[p-(trans-4-n-propylcyclohexyl)phenyl]-2-(3-fluoro-4-chlorophenyl)-ethene (obtained according to scheme 6) and customary work-up 1-[p-(trans-4-n-pro-pylcyclohexyl)-phenyl]-2-(3-fluoro-4-chlorophenyl)-ethane is obtained C 66.3 I.

EXAMPLE 41

A mixture of 0.1 mole of 1-chloro-2-fluoro-4-(trans-4-n-propylcyclohexylethyl)benzene (obtained by the reaction of 4-n-propylcyclohexylmethylphosphonium iodide with 4-chloro-3-fluorobenzaldehyde followed by hydrogenation), 0.1M 4-chlorophenylboronic acid (obtained by the reaction of 4-bromochlorobenzene with magnesium and trimethylborate), tetrakis(triphenylphosphine)palladium (1 mole %) 2m sodium carbonate solution (150 ml), toluene (250 ml) and IMS (60 ml) is stirred and refluxed for 16 hrs under a nitrogen atmosphere. After cooling the organic layer is separated, washed with water and the solvent evaporated off. The crude 4-(trans-4-propylcyclohexylethyl)-2-fluoro4'-chlorobiphenyl is purified by chromatography on silica and crystallisation.

EXAMPLE 42

STEP 1 AND STEP 2

Buryl lithium (1.6 m) (95 ml) was slowly added to trans 1,4-propylcyclohexylmethyl phosphonium iodide (70 g) in THF (140 ml) at 20° C. and stirred for 1 hr. 3-fluorobenzaldehyde (16.5 9) in THF (20 ml) was added dropwise and stirred for 15 mins. Water (100 ml) was added and the volatiles distilled off. Dichloromethane (200 ml) was added and the organic layer separated, washed with dilute hydrogenperoxide and then ammonium ferrous sulphate and water. Column chromatography gave the cis/trans alkene which was hydrogenated with Pd/C in THF (100 ml) to give the required ethane.

STEP 3

Product from step 2 ( 17.8 g) dissolved in THF (30 ml), potassium butoxide (8 g) in THF (30 ml) and DMPU (9.5 g) were cooled to −110° C. Buryl lithium (1.6 m) (50 ml) was added dropwise over 40 min and stirred at −100° C. for 1 hr. Trimethyl borate (8.2 g) in THF (20 ml) was added and the reaction mixture allowed to warm to 20° C. Normal work up gave the required boronic acid.

STEP 4

A mixture of boronic acid (1.9 g) from the previous step, 4-bromo-chlorobenzene (1.6 g), toluene (20 ml), ethanol (5 ml), palladium tetra (triphenylphosphine) (0.1 g) and sodium carbonate solution (10 ml) was stirred and heated at reflux for 5 hrs. The product was isolated by extraction and column chromatography to give 4-(trans-4-n-propylcyclohexyl-ethyl)-2-fluoro-4'-chlorobiphenyl.

EXAMPLE 43

STEP 1

The Grignard reagent of 4-bromo-chlorobenzene (75.9 g) was prepared by reaction with magnesium (8.3 g) in THF (515 ml), after cooling to 20° C., zinc chloride (315 ml of 1.0 m soln in diethyl ether) was added with cooling, excess magnesium was filtered off. This mixture was added to a mixture of 4-bromo-3-fluoro-1-iodobenzene (86.2 g) in THF (150 ml) containing palladium tetra (triphenylphosphine) (1.0 g) and stirred for 2 days under nitrogen. Normal workup and chromatography gave 4-bromo-2-fluoro-4'-chlorobiphenyl.

STEP 2

The product from step 1 (18.6 g) was converted to the Grignard reagent using magnesium (1.4 g) and THF (70 ml). Trans-4-pentylcyclohexanone (8.7 g) in THF (20 ml) was slowly added and the mixture then heated under reflux for 1 hr. After the usual workup 22.5 g of viscous oil was isolated, this was dehydrated using toluensulphonic acid (0.2 g) in toluene (100 ml) to give the alkene (Scheme 6). After hydrogenation of the double bond the trans-isomer was isolated by extraction and column chromatography to give 4-(trans-4-n-pentylcyclohexyl)-2-fluoro-4'-chlorobiphenyl.

EXAMPLE 44

A mixture of 0.1 mole of 1-chloro-4-[2-(4-(trans-4-n-propyl-cyclohexyl)-phenyl)-ethyl]-benzene (obtained by the reaction of 4-(trans-4-n-propylcyclohexyl)-benzylphosphonium iodide with 4-chlorobenzaldehyde followed by hydrogenation), 0.1 mole 4-chloro-3-fluorophenylboronic acid (obtained by the reaction of 1-bromo-3-fluoro-4-chlorobenzene with magnesium and trimethylborate), tetrakis (triphenylphosphine) palladium (1 mole %), 2 m sodium carbonate solution (150 ml), toluene (250 ml) and IMS (60 ml) is stirred and refluxed for 16 hrs. After cooling the organic layer is separated, washed with water and the solvent evaporated off.

The crude 1-[4-(trans-4-n-propylcyclohexyl)-phenyl]-2-(4'-chloro-3'-fluorobiphenyl-4-yl)-ethane is purified by chromatography on silica and crystallization, C 100 N 208 I.

We claim:

1. A benzene derivative of formula Ib

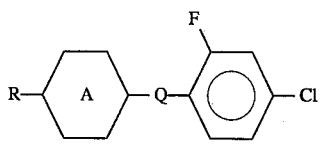

wherein

R denotes an alkyl or halogenoalkyl residue of up to 12 C atoms wherein one or two non-adjacent $CH_2$ groups may also be replaced by -O- and/or -HC=pH-, A is a ring of the formula (1)

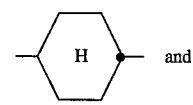 and

Q is 1,4-phenylene.

2. Liquid crystalline medium being a mixture of at least two compounds, characterized in that at least one compound is a benzene derivative according to claim 1.

3. Liquid crystal display device, characterized in that it contains a liquid crystalline medium according claim 1.

4. A benzene derivative of formula Ic

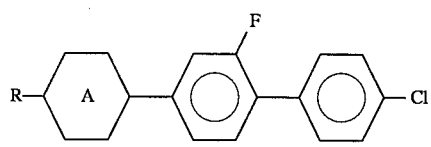

wherein R is an alkyl or halogenoalkyl residue of up to 12 C atoms wherein one or two non-adjacent $CH_2$ groups may also be replaced by -O- and/or -HC=CH-, and the radical A is trans-1,4-cyclohexylene or 1,4-phenylene.

5. A liquid crystalline medium being a mixture of at least two compounds, wherein at least one compound is a benzene derivative according to claim 4.

6. A liquid crystal display device containing a liquid crystalline medium according to claim 4.

7. A benzene derivative of formula Id

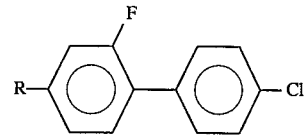

wherein R is an alkyl or halogenoalkyl residue of up to 12 C atoms wherein one or two non-adjacent $CH_2$ groups may also be replaced by -O- and/or -HC=CH-.

8. A liquid crystalline medium being a mixture of at least two compounds, wherein at least one compound is a benzene derivative according to claim 7.

9. A liquid crystal display device containing a liquid crystalline medium according to claim 7.

* * * * *